US007476669B2

(12) United States Patent
Chari et al.

(10) Patent No.: US 7,476,669 B2
(45) Date of Patent: Jan. 13, 2009

(54) CYTOTOXIC AGENTS COMPRISING TAXANES AND THEIR THERAPEUTIC USE

(75) Inventors: Ravi V. J. Chari, Newton, MA (US); Walter A. Blättler, Brookline, MA (US)

(73) Assignee: Immunogen Inc., Waltham, MA (US)

( * ) Notice: Subject to any disclaimer, the term of this patent is extended or adjusted under 35 U.S.C. 154(b) by 0 days.

(21) Appl. No.: 11/785,482

(22) Filed: Apr. 18, 2007

(65) Prior Publication Data

US 2007/0196332 A1 Aug. 23, 2007

Related U.S. Application Data

(62) Division of application No. 11/203,960, filed on Aug. 16, 2005, now Pat. No. 7,217,819, which is a division of application No. 10/684,746, filed on Oct. 15, 2003, now Pat. No. 7,008,942, which is a division of application No. 10/207,814, filed on Jul. 31, 2002, now Pat. No. 6,706,708, which is a division of application No. 10/059,022, filed on Jan. 30, 2002, now Pat. No. 6,436,931, which is a division of application No. 09/933,018, filed on Aug. 21, 2001, now Pat. No. 6,372,738, which is a division of application No. 09/717,026, filed on Nov. 22, 2000, now Pat. No. 6,340,701.

(60) Provisional application No. 60/167,228, filed on Nov. 24, 1999.

(51) Int. Cl.
*A61K 38/22* (2006.01)
*A61K 39/395* (2006.01)
*C07D 413/02* (2006.01)

(52) U.S. Cl. .............................. 514/232.2; 514/254.11; 514/320; 514/449; 544/147; 544/374; 546/196; 549/510; 549/511

(58) Field of Classification Search ............... 514/232.2, 514/254.11, 320, 449; 544/147, 374; 546/196; 549/510, 511
See application file for complete search history.

(56) References Cited

U.S. PATENT DOCUMENTS

| 5,399,726 | A | 3/1995 | Holton et al. |
| 5,416,064 | A | 5/1995 | Chari et al. |
| 5,475,011 | A | 12/1995 | Ojima et al. |
| 5,475,092 | A | 12/1995 | Chari et al. |
| 5,646,176 | A | 7/1997 | Golik et al. |
| 5,811,452 | A | 9/1998 | Ojima et al. |
| 5,824,701 | A | 10/1998 | Greenwald et al. |
| 6,175,023 | B1 | 1/2001 | Liu |
| 6,340,701 | B1 | 1/2002 | Chari et al. |

FOREIGN PATENT DOCUMENTS

| EP | 0624377 A2 | 5/1994 |
| EP | 1033372 A1 | 9/2000 |
| WO | WO 89/12624 A2 | 12/1989 |
| WO | WO 97/44026 A1 | 11/1997 |
| WO | WO 98/19705 A1 | 5/1998 |
| WO | WO 98/52614 A2 | 11/1998 |
| WO | WO 00/50059 A1 | 8/2000 |

OTHER PUBLICATIONS

Taxanes in Cancer Treatment [online], [retrieved on Feb. 28, 2007]. Retrieved from the internet, URL<http://cancerweb.ncl.ac.uk/cancernet/600715.html>.Feb. 28, 2007.*

GI50 Mean Graph for Compound 125973 [online], [retrieved on Feb. 21, 2007]. Retrieved from the internet, URL<http://dtp.nci.nih.gov/dtpstandard/servlet/MeanGraphSummary?testshortname=Cancer+Screen+09%2F2003+Data&searchtype=NSC&searchlist=125973>.*

Shoemaker, Robert H., Nature Reviews, vol. 6, Oct. 2006, pp. 813-823.*

Golik et al., "Synthesis and Antitumor Evaluation of Paclitaxel Phosphonooxymethyl Ethers: A Novel Class of Water Soluble Paclitaxel Pro-Drugs", Bioorganic & Medicinal Chemistry Letters, vol. 6. No. 15, pp. 1837-1842, 1996.

Huff, "HIV Protease: A Novel Chemotherapeutic Target for AIDS", Journal of Medicinal Chemistry, vol. 34, No. 8, pp. 2305-2314, (1991).

Lala et al., "Role of Nitric Oxide in Tumor Progression: Lessons from Experimental Tumors", Cancer and Metastasis Reviews (1998), 17(1), 91-106.

Golub et al., "Molecular Classification of Cancer: Class Discovery and Class Prediction by Gene Expression Monitoring", Science (1999), vol. 286, 531-537.

Ojima et al, "A Common Pharmacophore for Cytotoxic Natural Products that Stabilize Microtubules," Proc. Natl. Acad. Sci., USA, 96:4256-4261 (1999).

Michael L. Miller, et al. "Synthesis of potent taxoids for tumor-specific delivery using monoclonal antibodies" Bioorganic & Medicinal Chemistry Letters 14, 4079-4082 (2004).

Erkan Baloglu, et al. "Synthesis and biological evaluation of novel taxoids designed for targeted delivery to tumors," Bioorganic & Medicinal Chemistry Letters 14, 5885-5888 (2004).

(Continued)

Primary Examiner—Kamal A Saeed
(74) Attorney, Agent, or Firm—Sughrue Mion, PLLC

(57) ABSTRACT

A cytotoxic agent comprising one or more taxanes linked to a cell binding agent. A therapeutic composition for killing selected cell populations comprising: (A) a cytotoxic amount of one or more taxanes covalently bonded to a cell binding agent through a linking group, and (B) a pharmaceutically acceptable carrier, diluent or excipient. A method for killing selected cell populations comprising contacting target cells or tissue containing target cells with an effective amount of a cytotoxic agent comprising one or more taxanes linked to a cell binding agent. Novel sulfur-containing taxanes.

29 Claims, 7 Drawing Sheets

OTHER PUBLICATIONS

Michael L. Miller, et al. "Synthesis of Taxoids with Improved Cytotoxicity and Solubility for Use in Tumor-Specific Delivery," *J. Med. Chem.*, 47, 4802-4805 (2004).

Huff, "HIV Protease: A Novel Chemotherapeutic Target for AIDS," *Journal of Medicinal Chemistry*, vol. 34, No. 8, pp. 2305-2314 (1991).

Lala et al, "Role of nitric oxide in tumor progression: Lessons from experimental tumors," *Cancer and Metastasis Reviews* (1998), 17(1), 91-106.

Golub et al, "Molecular Classification of Cancer: Class Discovery and Class Prediction by Gene Expression Monitoring," *Science* (1999), vol. 286, 531-537.

Safavy et al, "Paclitaxel Derivatives for Targeted Therapy of Cancer: Toward the development of smart Taxanes," *Journal of Medicinal Chemistry*, 42, 4919-24 (1999).

Wang et al, Synthesis and Biological Activity of Advanced 2nd-Generation Taxoids, American Chemical Society Division of Medicinal Chemistry, Abstracts, 218th ACS National Meeting, Aug. 22-26, 1999 MEDI-038.

Ojima et al, "Syntheses and Structure-Activity Relationships of Taxoids Derived from 14-Hydroxy-10-deacetylbaccatin III," *J. Med. Chem.*, 40:267-278 (1997).

\* cited by examiner

| Compound | $R_1$ | $R_2$ | $R_3$ | $R_4$ | $R_5$ |
|---|---|---|---|---|---|
| Paclitaxel (Taxol) | -H | -COCH$_3$ | -C$_6$H$_5$ | -C$_6$H$_5$ | H |
| Docetaxel (Taxotere) | -H | -H | -C$_6$H$_5$ | -OC(CH$_3$)$_3$ | H |
| More Potent Taxanes | -F | -COCH$_2$CH$_3$ | -CH$_2$CH(CH$_3$)$_2$ | -OC(CH$_3$)$_3$ | H |
| | -F | -COCH$_2$CH$_3$ | -CH=C(CH$_3$)$_2$ | -OC(CH$_3$)$_3$ | H |
| | -Cl | -COCH$_2$CH$_3$ | -CH$_2$CH(CH$_3$)$_2$ | -OC(CH$_3$)$_3$ | H |
| | -OCH$_3$ | -COCH$_3$ | -CH$_2$CH(CH$_3$)$_2$ | -OC(CH$_3$)$_3$ | H |

Figure 2

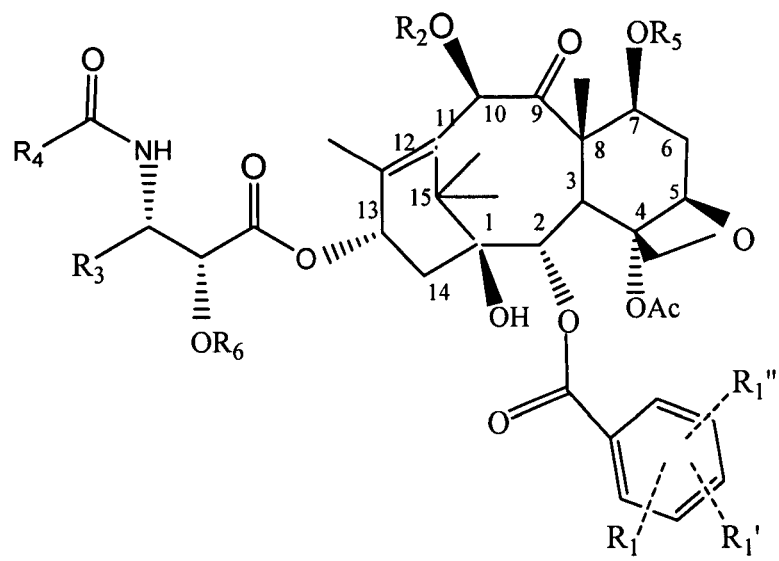

|   | R₁ | R₂ | R₃ | R₄ | R₅ | R₆ |
|---|---|---|---|---|---|---|
| 1 | -F | -COCH₂CH₃<br>-CH₂CH₃, or<br>-CONHCH₂CH₃ | -CH₂CH(CH₃)₂<br>or –C₆H₅ | -OC(CH₃)₃<br>or –C₆H₅ | -CH₂CH₂SH or<br>-COCH₂CH₂SH | -COCH₂CH₃,<br>-CH₂CH₃, or<br>-CONHCH₂CH₃ |
| 2 | -F | -COCH₂CH₃,<br>-CH₂CH₃, or<br>-CONHCH₂CH₃ | -CH=C(CH₃)₂<br>or –C₆H₅ | -OC(CH₃)₃<br>or –C₆H₅ | -CH₂CH₂SH or<br>-COCH₂CH₂SH | -COCH₂CH₃,<br>-CH₂CH₃, or<br>-CONHCH₂CH₃ |
| 3 | -F | -COCH₂CH₂SH<br>-CH₂CH₂SH | -CH₂CH(CH₃)₂<br>or –C₆H₅ | -OC(CH₃)₃<br>or –C₆H₅ | -COCH₂CH₃,<br>-CH₂CH₃, or<br>-CONHCH₂CH₃ | -COCH₂CH₃,<br>-CH₂CH₃, or<br>-CONHCH₂CH₃ |
| 4 | -F | -COCH₂CH₃,<br>-CH₂CH₃, or<br>-CONHCH₂CH₃ | -CH₂CH(CH₃)₂<br>or –C₆H₅ | -OC(CH₃)₃<br>or –C₆H₅ | -COCH₂CH₃,<br>-CH₂CH₃, or<br>-CONHCH₂CH₃ | -CH₂CH₂SH or<br>-COCH₂CH₂SH |

CYTOTOXIC AGENTS COMPRISING TAXANES AND THEIR THERAPEUTIC USE

This application is a divisional of U.S. application Ser. No. 11/203,960 (Confirmation No. 2430) filed Aug. 16, 2005 now U.S. Pat. No. 7,217,819 (allowed), which is a divisional of U.S. application Ser. No. 10/684,746 (Confirmation No. 4047) filed Oct. 15, 2003 (U.S. Pat. No. 7,008,942), which is a divisional of U.S. application Ser. No. 10/207,814 (Confirmation No. 3691) filed Jul. 31, 2002 (U.S. Pat. No. 6,706,708), which is a divisional of U.S. application Ser. No. 10/059,022 (Confirmation No. 8545) filed Jan. 30, 2002 (U.S. Pat. No. 6,436,931), which is a divisional of U.S. application Ser. No. 09/933,018 (Confirmation No. 6969) filed Aug. 21, 2001 (U.S. Pat. No. 6,372,738), which is a divisional of U.S. Application of 09/717,026 (Confirmation No. 8520) filed Nov. 22, 2000 (U.S. Pat. No. 6,340,701); which claims benefit of Provisional Application No. 60/167,228, filed Nov. 24, 1999, the disclosure of each of which is incorporated herein by reference in its entirety.

FIELD OF THE INVENTION

The present invention relates to novel cytotoxic agents and their therapeutic use. More specifically, the invention relates to novel cytotoxic agents comprising taxanes and their therapeutic use. These novel cytotoxic agents have therapeutic use as a result of delivering the taxanes to a specific cell population in a targeted fashion by chemically linking the taxane to a cell binding agent.

BACKGROUND OF THE INVENTION

Many reports have appeared on the attempted specific targeting of tumor cells with monoclonal antibody-drug conjugates (Sela et al, in *Immunoconjugates* 189-216 (C. Vogel, ed. 1987); Ghose et al, in *Targeted Drugs* 1-22 (E. Goldberg, ed. 1983); Diener et al, in *Antibody mediated delivery systems* 1-23 (J. Rodwell, ed. 1988); Pietersz et al, in *Antibody mediated delivery systems* 25-53 (J. Rodwell, ed. 1988); Bumol et al, in *Antibody mediated delivery systems* 55-79 (J. Rodwell, ed. 1988). All references and patents cited herein are incorporated by reference.

Cytotoxic drugs such as methotrexate, daunorubicin, doxorubicin, vincristine, vinblastine, melphalan, mitomycin C, and chlorambucil have been conjugated to a variety of murine monoclonal antibodies. In some cases, the drug molecules were linked to the antibody molecules through an intermediary carrier molecule such as serum albumin (Garnett et al, 46 *Cancer Res.* 2407-2412 (1986); Ohkawa et al 23 *Cancer Immunol. Immunother.* 81-86 (1986); Endo et al, 47 *Cancer Res.* 1076-1080 (1980)), dextran (Hurwitz et al, 2 *Appl. Biochem.* 25-35 (1980); Manabi et al, 34 *Biochem. Pharmacol.* 289-291 (1985); Dillman et al, 46 *Cancer Res.* 4886-4891 (1986); Shoval et al, 85 *Proc. Natl. Acad. Sci.* 8276-8280 (1988)), or polyglutamic acid (Tsukada et al, 73 *J. Natl. Canc. Inst.* 721-729 (1984); Kato et al 27 *J. Med. Chem.* 1602-1607 (1984); Tsukada et al, 52 *Br. J. Cancer* 111-116 (1985)).

A wide array of linker technologies has been employed for the preparation of such immunoconjugates and both cleavable and non-cleavable linkers have been investigated. In most cases, the full cytotoxic potential of the drugs could only be observed, however, if the drug molecules could be released from the conjugates in unmodified form at the target site.

One of the cleavable linkers that has been employed for the preparation of antibody-drug conjugates is an acid-labile linker based on cis-aconitic acid that takes advantage of the acidic environment of different intracellular compartments such as the endosomes encountered during receptor mediated endocytosis and the lysosomes. Shen and Ryser introduced this method for the preparation of conjugates of daunorubicin with macromolecular carriers (102 *Biochem. Biophys. Res. Commun.* 1048-1054 (1981)). Yang and Reisfeld used the same technique to conjugate daunorubicin to an anti-melanoma antibody (80 *J. Natl. Canc. Inst.* 1154-1159 (1988)). Dillman et al. also used an acid-labile linker in a similar fashion to prepare conjugates of daunorubicin with an anti-T cell antibody (48 *Cancer Res.* 6097-6102 (1988)).

An alternative approach, explored by Trouet et al, involved linking daunorubicin to an antibody via a peptide spacer arm (79 *Proc. Natl. Acad. Sci.* 626-629 (1982)). This was done under the premise that free drug could be released from such a conjugate by the action of lysosomal peptidases.

In vitro cytotoxicity tests, however, have revealed that antibody-drug conjugates rarely achieved the same cytotoxic potency as the free unconjugated drugs. This suggested that mechanisms by which drug molecules are released from the antibodies are very inefficient. In the area of immunotoxins, conjugates formed via disulfide bridges between monoclonal antibodies and catalytically active protein toxins were shown to be more cytotoxic than conjugates containing other linkers. See, Lambert et al, 260 *J. Biol. Chem.* 12035-12041 (1985); Lambert et al, in *Immunotoxins* 175-209 (A. Frankel, ed. 1988); Ghetie et al, 48 *Cancer Res.* 2610-2617 (1988). This was attributed to the high intracellular concentration of glutathione contributing to the efficient cleavage of the disulfide bond between an antibody molecule and a toxin. Despite this, there are only a few reported examples of the use of disulfide bridges for the preparation of conjugates between drugs and macromolecules. Shen et al (260 *J. Biol. Chem.* 10905-10908 (1985)) described the conversion of methotrexate into a mercaptoethylamide derivative followed by conjugation with poly-D-lysine via a disulfide bond. Another report described the preparation of a conjugate of the trisulfide containing toxic drug calicheamycin with an antibody (Hinman et al., 53 *Cancer Res.* 3336-3342 (1993)).

One reason for the lack of disulfide linked antibody-drug conjugates is the unavailability of cytotoxic drugs possessing a sulfur atom containing moiety that can be readily used to link the drug to an antibody via a disulfide bridge. Furthermore, chemical modification of existing drugs is difficult without diminishing their cytotoxic potential.

Another major drawback with existing antibody-drug conjugates is their inability to deliver a sufficient concentration of drug to the target site because of the limited number of targeted antigens and the relatively moderate cytotoxicity of cancerostatic drugs like methotrexate, daunorubicin, and vincristine. In order to achieve significant cytotoxicity, linkage of a large number of drug molecules, either directly to the antibody or through a polymeric carrier molecule, becomes necessary. However, such heavily modified antibodies often display impaired binding to the target antigen and fast in vivo clearance from the blood stream.

In spite of the above described difficulties, useful cytotoxic agents comprising cell binding moieties and the group of cytotoxic drugs known as maytansinoids have been reported (U.S. Pat. No. 5,208,020, U.S. Pat. No. 5,416,064, and R. V. J. Chari, 31 *Advanced Drug Delivery Reviews* 89-104 (1998)). Similarly, useful cytotoxic agents comprising cell binding moieties and analogues and derivatives of the potent antitumor antibotic CC-1065 have also been reported (U.S. Pat. No. 5,475,092 and U.S. Pat. No. 5,585,499).

Paclitaxel (Taxol), a cytotoxic natural product, and docetaxel (Taxotere), a semi-synthetic derivative (See FIG. 1), are widely used in the treatment of cancer. These compounds belong to the family of compounds called taxanes. Taxanes are mitotic spindle poisons that inhibit the depolymerization of tubulin, resulting in an increase in the rate of microtubule assembly and cell death. While docetaxel and paclitaxel are useful agents in the treatment of cancer, their antitumor activity is limited because of their non-specific toxicity towards normal cells.

Further, compounds like paclitaxel and docetaxel themselves are not sufficiently potent to be used in conjugates of cell binding agents. Recently, a few new docetaxel analogs with greater potency than either docetaxel or paclitaxel have been described (Wang, T.; Miller, M.; Borella, C.; Lin, S.; Geng, X.; Pera, P.; Bemacki, R. J.; Ojima, I., Syntheses and biological activity of advanced second-generation taxoids, 218$^{th}$ ACS National Meeting, Aug. 22-26 1999, MEDI-038 and FIG. 1). However, these compounds lack a suitable functionality that allows linkage via a cleavable bond to cell binding agents.

Accordingly, a method of treating diseases with taxanes wherein their side effects are reduced without compromising their cytotoxicity is greatly needed.

SUMMARY OF THE INVENTION

One object of the present invention is to provide taxanes that are highly toxic and that can still be effectively used in the treatment of many diseases.

Another object of the present invention is to provide novel taxanes.

These and other objects have been achieved by providing a cytotoxic agent comprising one or more taxanes linked to a cell binding agent.

In a second embodiment, the present invention provides a therapeutic composition comprising:

(A) an effective amount of one or more taxanes linked to a cell binding agent, and (B) a pharmaceutically acceptable carrier, diluent, or excipient.

In a third embodiment, the present invention provides a method of killing selected cell populations comprising contacting target cells or tissue containing target cells, with a cytotoxic amount of a cytotoxic agent comprising one or more taxanes linked to a cell binding agent.

In a fourth embodiment, the present invention provides taxanes comprising a linking group capable of linking said taxanes to a cell binding agent or other chemical moieties.

BRIEF DESCRIPTION OF THE DRAWINGS

FIG. 2 is a chemical formula that represents structures of some of the disulfide-containing taxanes according to the present invention.

DETAILED DESCRIPTION OF THE INVENTION

Figure 1:
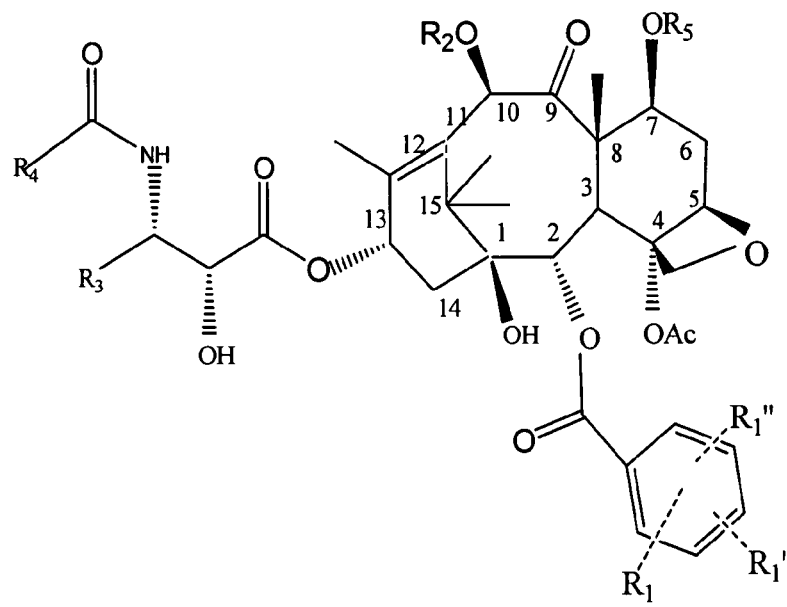
FIG. 1 is a chemical formula that represents structures of various taxanes, including some of the more potent taxanes described by Wang et al., supra.

This invention is based on the synthesis of novel taxanes that retain high cytotoxicity and that can be effectively linked to cell binding agents. It has previously been shown that the linkage of highly cytotoxic drugs to antibodies using a cleavable link, such as a disulfide bond, ensures the release of fully active drug inside the cell, and such conjugates are cytotoxic in an antigen specific manner (R. V. J. Chari et al, 52 Cancer Res. 127-131 (1992); U.S. Pat. No. 5,475,092; and U.S. Pat. No. 5,416,064). However, the art reveals that it is extremely difficult to modify existing drugs without diminishing their cytotoxic potential. The disclosed invention overcomes this problem by modifying the disclosed taxanes with chemical moieties, and especially ones containing thiol or disulfide groups, to which appropriate cell binding agents can be linked. As a result, the disclosed novel taxanes preserve, and in some cases could even enhance, the cytotoxic potency of known taxanes. The cell binding agent-taxane complexes permit the full measure of the cytotoxic action of the taxanes to be applied in a targeted fashion against unwanted cells only, therefore, avoiding side effects due to damage to non-targeted healthy cells. This invention permits the taxanes to be target site-directed which had previously been impossible. Thus, the invention provides useful agents for the elimination of diseased or abnormal cells that are to be killed or lysed such as tumor cells (particularly solid tumor cells), virus infected cells, microorganism infected cells, parasite infected cells, autoimmune cells (cells that produce autoantibodies), activated cells (those involved in graft rejection or graft vs. host disease), or any other type of diseased or abnormal cells, while exhibiting a minimum of side effects.

The cytotoxic agent according to the present invention comprises one or more taxanes linked to a cell binding agent via a linking group. The linking group is part of a chemical moiety that is covalently bound to a taxane through conventional methods. In a preferred embodiment, the chemical moiety can be covalently bound to the taxane via an ether linkage.

The taxanes useful in the present invention have the formula (I) shown below:

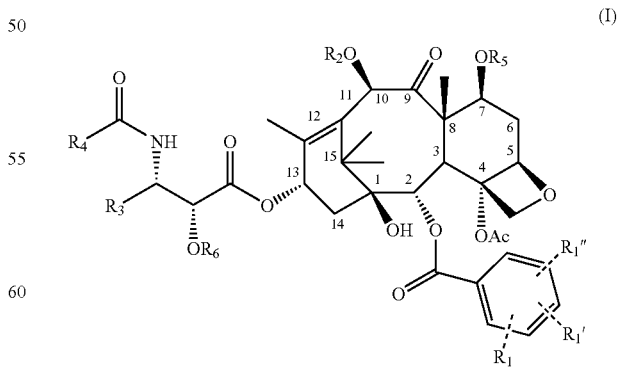

(I)

These novel taxanes can be divided into four embodiments, (1), (2), (3) and (4), respectively. Examples of the four embodiments are shown in FIG. 2.

In embodiments (1) to (4), $R_1$ is an electron withdrawing group, such as —F, —$NO_2$, —CN, —Cl, —$CHF_2$, or —$CF_3$ or an electron donating group such as —$OCH_3$, —$OCH_2CH_3$, —$NR_7R_8$, or —$OR_9$, and $R_1'$ and $R_1''$ are the same or different and are H, an electron withdrawing group, or an electron donating group. $R_1$ can also be H.

$R_7$ and $R_8$ are the same or different and are linear alkyl having 1 to 10 carbon atoms, branched or cyclic alkyl having 3 to 10 carbon atoms, or simple or substituted aryl having 1 to 10 carbon atoms. Preferably the number of carbon atoms for $R_7$ and $R_8$ is 1 to 4. Also, preferably $R_7$ and $R_8$ are the same. Examples of preferred —$NR_7R_8$ groups include dimethyl amino, diethyl amino, dipropyl amino, and dibutyl amino, where the butyl moiety is any of primary, secondary, tertiary or isobutyl. $R_9$ is linear alkyl having 1 to 10 carbon atoms, or branched or cyclic alkyl having 3 to 10 carbon atoms.

$R_1$ is preferably —F, —$NO_2$ or —$CF_3$.

Preferably, $R^1$ is in the meta position and $R^{1'}$ and $R^{1'''}$ are H.

In embodiments (1), (2) and (4), $R_2$ is heterocyclic, together with the oxygen atom at the C-10 position forms a linear ester or ether having from 1 to 10 carbon atoms, or a branched or cyclic ester or ether having from 3 to 10 carbon atoms, or a carbamate of the formula —$CONR_{10}R_{11}$, wherein $R_{10}$ and $R_{11}$ are the same or different and are H, linear alkyl having 1 to 10 carbon atoms, branched or cyclic alkyl having 3 to 10 carbon atoms, or simple or substituted aryl having 1 to 10 carbon atoms. For esters, preferred examples of $R_2$ include —$COCH_2CH_3$ and —$COCH_2CH_2CH_3$. For carbamates, preferred examples of $R_2$ include —$CONHCH_2CH_3$, —$CONHCH_2CH_2CH_3$, —CO-morpholino, —CO-piperazino, —CO-piperidino, or —CO—N-methylpiperazino.

In embodiment (3), $R_2$ is the linking group.

In embodiments (1), (3) and (4), $R_3$ is aryl, linear alkyl having 1 to 10 carbon atoms, or branched or cyclic alkyl having 3 to 10 carbon atoms, preferably, —$CH_2CH(CH_3)_2$.

In embodiment (2), $R_3$ is —CH=C(CH_3)_2.

In all embodiments, $R_4$ is —$OC(CH_3)_3$ or —$C_6H_5$.

In embodiments (1) and (2), $R_5$ is the linking group, and $R_6$ is H or has the same definition as above for $R_2$ for embodiments (1), (2) and (4).

In embodiment (3), $R_5$ is H or has the same definition as above for $R_2$ for embodiments (1), (2) and (4).

In embodiment (3), $R_6$ is H or has the same definition as above for $R_2$ for embodiments (1), (2) and (4).

In embodiment (4), $R_5$ is H or has the same definition as above for $R_2$ for embodiments (1), (2) and (4), and $R_6$ is a linking group.

The preferred positions for introduction of the linking group are $R_2$ and $R_5$, with $R_2$ being the most preferred. Suitable linking groups are well known in the art and include disulfide groups, thioether groups, acid labile groups, photolabile groups, peptidase labile groups and esterase labile groups. Preferred are disulfide groups and thioether groups.

When the linking group is a thiol- or disulfide-containing group, the side chain carrying the thiol or disulfide group can be linear or branched, aromatic or heterocyclic. One of ordinary skill in the art can readily identify suitable side chains. Specific examples of the thiol- or disulfide-containing substituents include —$(CH_2)_nSZ$, —$CO(CH_2)_nSZ$, —$(CH_2)_nCH(CH_3)SZ$, —$CO(CH_2)_nCH(CH_3)SZ$, —$(CH_2)_nC(CH_3)_2SZ$, —$CO(CH_2)_nC(CH_3)_2SZ$, —$CONR_{12}(CH_2)_nSZ$, —$CONR_{12}(CH_2)_nCH(CH_3)SZ$, or —$CONR_{12}(CH_2)_nC(CH_3)_2SZ$, —CO-morpholino-XSZ, —CO-piperazino-XSZ, —CO-piperidino-XSZ, and —CO—N-methylpiperazino-XSZ, wherein Z is H or SR, X is linear alkyl having 1-10 carbon atoms or branched alkyl having 3-10 carbon atoms, R and $R_{12}$ are the same or different and are linear alkyl having 1 to 10 carbon atoms, branched or cyclic alkyl having 3 to 10 carbon atoms, or simple or substituted aryl having from 1 to 10 carbon atoms or heterocyclic, and $R_{12}$ can in addition be H, and n is an integer of 1 to 10.

Examples of linear alkyls include methyl, ethyl, propyl, butyl, pentyl and hexyl.

Examples of branched alkyls include isopropyl, isobutyl, sec.-butyl, tert.-butyl, isopentyl and 1-ethyl-propyl.

Examples of cyclic alkyls include cyclopropyl, cyclobutyl, cyclopentyl and cyclohexyl.

Examples of simple aryls include phenyl and naphthyl.

Examples of substituted aryls include aryls such as those described above substituted with alkyl groups, with halogens, such as —Cl, —Br or —F, nitro groups, amino groups, sulfonic acid groups, carboxylic acid groups, hydroxy groups or alkoxy groups.

Examples of heterocyclics are compounds wherein the heteroatoms are selected from O, N, and S, and include morpholino, piperidino, piperazino, N-methylpiperazino, pyrrolyl, pyridyl, furyl and thiophene.

The taxanes of the present invention that have a thiol- or disulfide-containing substituent are in themselves novel.

Figure 3:
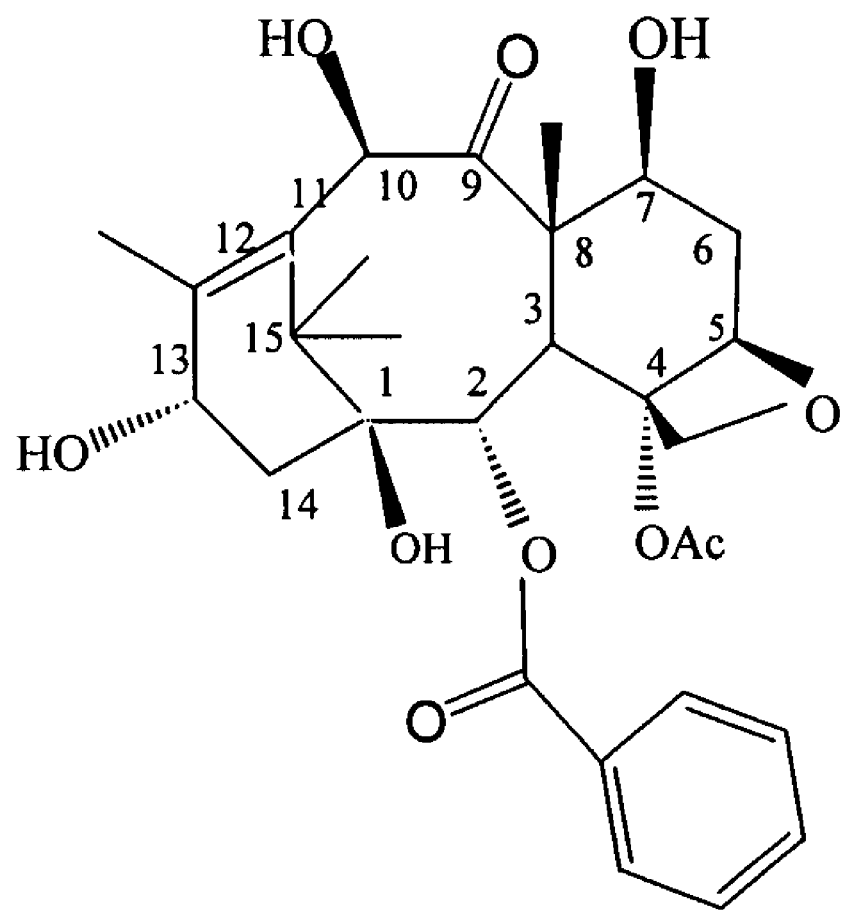
FIG. 3 shows the structure of 10-deacetylbaccatin III, which is the starting material for preparing taxanes.

The taxanes that have a thiol or disulfide-containing substituent can be synthesized according to known methods. The starting material for the synthesis is the commercially available 10-deacetylbaccatin III, shown in FIG. 3. The chemistry to introduce various substituents is described in several publications (Ojima et al, *J. Med. Chem.* 39, 3889-3896, (1996), Ojima et al., 40 *J. Med. Chem.* 267-278 (1997); I. Ojima et al., 96 *Proc. Natl. Acad. Sci.,* 4256-4261 (1999); I. Ojima et al., U.S. Pat. No. 5,475,011 and U.S. Pat. No. 5,811,452.).

The substituent $R_1$ on the phenyl ring and the position of the substituent $R_1$ can be varied until a compound of the desired toxicity is obtained. Furthermore, the degree of substitution on the phenyl ring can be varied to achieve a desired toxicity. That is, the phenyl ring can have one or more substituents (e.g., mono-, di-, or tri-substitution of the phenyl ring) which provide another means for achieving a desired toxicity. High cytotoxicity is defined as exhibiting a toxicity having an $IC_{50}$ in the range of $1\times10^{-12}$ to $3\times10^{-9}$M, when measured in vitro with cultured cancer cells upon a 72 hour exposure time to the drug. One of ordinary skill in the art can determine the appropriate chemical moiety for $R_1$ and the appropriate position for $R_1$ using only routine experimentation.

For example electron withdrawing groups at the meta position are expected to increase the cytotoxic potency, while substitution at the para position is not expected to increase the potency as compared to the parent taxane. Typically a few representative taxanes with substituents at the different positions (ortho, meta and para) will be initially prepared and evaluated for in vitro cytotoxicity.

The disulfide or thiol-containing substituent can be introduced at one of the positions where a hydroxyl group already exists. The chemistry to protect the various hydroxyl groups, while reacting the desired one, has been described previously (see, for example, the references cited supra). The substituent is introduced by simply converting the free hydroxyl group to a disulfide-containing ether, a disulfide-containing ester, or a disulfide-containing carbamate. This transformation is achieved as follows. The desired hydroxyl group is deprotonated by treatment with the commercially available reagent lithium hexamethyldisilazane (1.2 equivalents) in tetrahydrofuran at −40° C. as described in I. Ojima et al, supra. The resulting alkoxide anion is then reacted with an excess of a dihalo compound, such as dibromoethane, to give a halo ether. Displacement of the halogen with a thiol (by reaction with potassium thioacetate and treatment with mild base or hydroxylamine) will provide the desired thiol-containing taxane. The thiol group can be converted into a methyl or pyridyl disulfide by reaction with methyl methane thiol sulfonate or dithiodipyridine respectively. This method is described in U.S. Pat. No. 5,416,064.

Alternatively, the desired hydroxyl group can be esterified directly by reaction with an acyl halide, such as 3-bromopropionyl chloride to give a bromo ester. Displacement of the bromo group by treatment with potassium thioacetate and further processing as described above will provide the thiol or disulfide-containing taxane ester. In order to prepare disulfide-containing carbamates, the hydroxyl group can be reacted with a commercially available chloroformate, such as para-nitrophenyl chloroformate followed by reaction with an amino alkyl disulfide (e.g., methyldithio cysteamine).

Disulfide-containing and thiol-containing taxane drugs of the invention can be evaluated for their ability to suppress proliferation of various unwanted cell lines in vitro. For example, cell lines such as the human epidermoid carcinoma line A431, the human breast tumor line SKBR3, and the Burkitt's lymphoma line Namalwa can easily be used for the assessment of cytotoxicity of these compounds. Cells to be evaluated can be exposed to the compounds for 72 hours and the surviving fractions of cells measured in direct assays by known methods. $IC_{50}$ values can then be calculated from the results of the assays.

The effectiveness of the compounds of the invention as therapeutic agents depends on the careful selection of an appropriate cell binding agent. Cell binding agents may be of any kind presently known, or that become known and include peptides and non-peptides. Generally, these can be antibodies, or fragments thereof, (especially monoclonal antibodies), lymphokines, hormones, growth factors, vitamins, nutrient-transport molecules (such as transferrin), or any other cell binding molecule or substance.

More specific examples of cell binding agents that can be used include:

- fragments of antibodies such as sFv, Fab, Fab', and F(ab')$_2$ (Parham, 131 *J. Immunol.* 2895-2902 (1983); Spring et al, 113 *J. Immunol.* 470-478 (1974); Nisonoff et al, 89 *Arch. Biochem. Biophys.* 230-244 (1960));
- interferons (e.g. α, β, γ);
- lymphokines such as IL-2, IL-3, IL-4, IL-6;
- hormones such as insulin, TRH (thyrotropin releasing hormones), MSH (melanocyte-stimulating hormone), steroid hormones, such as androgens and estrogens;
- vitamins such as folic acid;
- growth factors and colony-stimulating factors such as EGF, TGF-α, G-CSF, M-CSF and GM-CSF (Burgess, 5 *Immunology Today* 155-158 (1984)); and
- transferrin (O'Keefe et al, 260 *J. Biol. Chem.* 932-937 (1985)).

Monoclonal antibody techniques allow for the production of extremely specific cell binding agents in the form of specific monoclonal antibodies or fragments thereof. Particularly well known in the art are techniques for creating monoclonal antibodies, or fragments thereof, by immunizing mice, rats, hamsters, or any other mammal with the antigen of interest such as the intact target cell, antigens isolated from the target cell, whole virus, attenuated whole virus, and viral proteins such as viral coat proteins. Sensitized human cells can also be used. Another method of creating monoclonal antibodies, or fragments thereof, is the use of phage libraries of sFv (single chain variable region), specifically human sFv. (See e.g., Griffiths et al., U.S. Pat. No. 5,885,793; McCafferty et al., WO 92/01047; Liming et al., WO 99/06587.)

Selection of the appropriate cell binding agent is a matter of choice that depends upon the particular cell population to be targeted, but in general monoclonal antibodies are preferred if an appropriate one is available.

For example, the monoclonal antibody J5 is a murine $IgG_{2a}$ antibody that is specific for Common Acute Lymphoblastic Leukemia Antigen (CALLA) (Ritz et al, 283 *Nature* 583-585 (1980)) and can be used if the target cells express CALLA such as in the disease of acute lymphoblastic leukemia. Similarly, the monoclonal antibody anti-B4 is a murine $IgG_1$, that binds to the CD19 antigen on B cells (Nadler et al, 131 *J. Immunol.* 244-250 (1983)) and can be used if the target cells are B cells or diseased cells that express this antigen such as in non-Hodgkin's lymphoma or chronic lymphoblastic leukemia.

Additionally, GM-CSF which binds to myeloid cells can be used as a cell binding agent to diseased cells from acute myelogenous leukemia. IL-2 which binds to activated T-cells can be used for prevention of transplant graft rejection, for therapy and prevention of graft-versus-host disease, and for treatment of acute T-cell leukemia. MSH which binds to melanocytes can be used for the treatment of melanoma. Folic acid, which targets the folate receptor expressed on ovarian and other cancers, is also a suitable cell binding agent.

Cancers of the breast and testes can be successfully targeted with estrogen (or estrogen analogues) or androgen (or androgen analogues) respectively as cell binding agents.

Conjugates of the taxanes of the invention and a cell binding agent can be formed using any techniques presently known or later developed. Numerous methods of conjugation are taught in U.S. Pat. No. 5,416,064 and U.S. Pat. No. 5,475,092. The taxane ester can be modified to yield a free amino group and then linked to an antibody or other cell binding agent via an acid labile linker or a photolabile linker. The taxane ester can be condensed with a peptide and subsequently linked to a cell binding agent to produce a peptidase labile linker. The hydroxyl group on the taxane ester can be succinylated and linked to a cell binding agent to produce a conjugate that can be cleaved by intracellular esterases to liberate free drug. Most preferably, the taxane ethers, esters, or carbamates are treated to create a free or protected thiol group, and then the disulfide- or thiol-containing taxanes are linked to the cell binding agent via disulfide bonds.

Representative conjugates of the invention are antibody-taxane, antibody fragment-taxane epidermal growth factor (EGF)-taxane, melanocyte stimulating hormone (MSH)-taxane, thyroid stimulating hormone (TSH)-taxane, estrogen-taxane, estrogen analogue-taxane, androgen-taxane, androgen analogue-taxane, and folate-taxane.

Taxane conjugates of antibodies, antibody fragments, protein or peptide hormones, protein or peptide growth factors and other proteins are made in the same way by known methods. For example, peptides and antibodies can be modified with cross linking reagents such as N-succinimidyl 3-(2-pyridyldithio)propionate, N-succinimidyl 4-(2-pyridyldithio)pentanoate (SPP), 4-succinimidyl-oxycarbonyl-α-methyl-α-(2-pyridyl dithio)-toluene (SMPT), N-succinimidyl-3-(2-pyridyldithio)butyrate (SDPB), 2-iminothiolane, or S-acetylsuccinic anhydride by known methods. See, Carlsson et al, 173 *Biochem. J.* 723-737 (1978); Blattler et al, 24 *Biochem.* 1517-1524 (1985); Lambert et al, 22 *Biochem.* 3913-3920 (1983); Klotz et al, 96 *Arch. Bio-* chem. Biophys. 605 (1962); and Liu et al, 18 Biochem. 690 (1979), Blakey and Thorpe, 1 *Antibody, Immunoconjugates & Radiopharmaceuticals,* 1-16 (1988), Worrell et al 1 *Anti-Cancer Drug Design* 179-184 (1986). The free or protected thiol-containing cell binding agent thus derived is then reacted with a disulfide- or thiol-containing taxane to produce conjugates. The conjugates can be purified by HPLC or by gel filtration.

Similarly, for example, estrogen and androgen cell binding agents such as estradiol and androstenediol can be esterified at the C-17 hydroxy group with an appropriate disulfide containing carboxylic acid using e.g., dicyclohexylcarbodiimide as a condensing agent. Examples of such carboxylic acids that can be employed are 3-(2-pyridyldithio) propanoic acid, 3-methyldithiopropanoic acid, 4-(2-pyridyldithio)pentanoic acid, and 3-phenyldithiopropanoic acid. Esterification of the C-17 hydroxy group can also be achieved by reaction with an appropriately protected thiol group containing carboxylic acid chloride such as 3-S-acetylpropanoyl chloride. Other methods of esterification can also be employed as described in the literature (Haslam, 36 *Tetrahedron* 2409-2433 (1980)). The protected or free thiol containing androgen or estrogen can then be reacted with a disulfide- or thiol-containing taxane to produce conjugates. The conjugates can be purified by column chromatography on silica gel or by HPLC. Folic acid can be condensed with a suitable hydrazide such as 4-(2-pyridyldithio) pentanoic acid hydrazide in the presence of a condensing agent such as dicyclohexyl carbodiimide to give a hydrazone containing an active disulfide. The disulfide-containing folate can then be reacted with a thiol-containing taxane to produce a conjugate that can be purified by column chromatography over silica gel or by HPLC.

Preferably monoclonal antibody- or cell binding agent-taxane conjugates are those that are joined via a disulfide bond, as discussed above, that are capable of delivering taxane molecules. Such cell binding conjugates are prepared by known methods such as by modifying monoclonal antibodies with succinimidyl pyridyl-dithiopropionate (SPDP) (Carlsson et al, 173 *Biochem. J.* 723-737 (1978)). The resulting thiopyridyl group is then displaced by treatment with thiol-containing taxanes to produce disulfide linked conjugates. Alternatively, in the case of the aryldithio-taxanes, the formation of the cell binding conjugate is effected by direct displacement of the aryl-thiol of the taxane by sulfhydryl groups previously introduced into antibody molecules. Conjugates containing 1 to 10 taxane drugs linked via a disulfide bridge are readily prepared by either method.

More specifically, a solution of the dithiopyridyl modified antibody at a concentration of 1 mg/ml in 0.1 M potassium phosphate buffer, at pH 6.5 containing 1 mM EDTA is treated with the thiol-containing taxane (1.25 molar eq./dithiopyridyl group). The release of thiopyridine from the modified antibody is monitored spectrophotometrically at 343 nm and is complete in about 20 hours. The antibody-taxane conjugate is purified and freed of unreacted drug and other low molecular weight material by gel filtration through a column of Sephadex G-25 or Sephacryl S300. The number of taxane moieties bound per antibody molecule can be determined by measuring the ratio of the absorbance at 230 nm and 275 nm. An average of 1-10 taxane molecules/antibody molecule can be linked via disulfide bonds by this method.

Antibody-taxane conjugates with non-cleavable links can also be prepared. The antibody can be modified with crosslinking reagents such as succinimidyl 4-(maleimidomethyl)cyclohexane-1-carboxylate (SMCC), sulfo-SMCC, m-maleimidobenzoyl-N-hydroxysuccinimide ester (MBS), sulfo-MBS or succinimidyl-iodoacetate, as described in the literature, to introduce 1-10 reactive groups. See, Yoshitake et al, 101 *Eur. J. Biochem.* 395-399 (1979); Hashida et al, *J. Applied Biochem.* 56-63 (1984); and Liu et al, 18 *Biochem.* 690-697 (1979). The modified antibody is then reacted with the thiol-containing taxane derivative to produce a conjugate. The conjugate can be purified by gel filtration through a Sephadex G-25 column.

The modified antibodies, or fragments thereof, are treated with the thiol-containing taxanes (1.25 molar equivalent/maleimido group). The mixtures are incubated overnight at about 4° C. The antibody-taxane conjugates are purified by gel filtration through a Sephadex G-25 column. Typically, an average of 1 to 10 taxanes per antibody are linked.

A preferred method is to modify antibodies, or fragments thereof, with succinimidyl-4-(maleimidomethyl)-cyclohexane-1-carboxylate (SMCC) to introduce maleimido groups followed by reaction of the modified antibody or fragment with the thiol-containing taxanes to give a thioether linked conjugate. Again, conjugates with 1 to 10 drug molecules per antibody molecule result.

Cytotoxicity of the taxanes and their antibody conjugates to non-adherent cell lines such as Namalwa and HL-60 can be measured by back-extrapolation of cell proliferation curves as described in Goldmacher et al, 135 *J. Immunol.* 3648-3651 (1985). Cytotoxicity of these compounds to adherent cell lines such as SKBR3 and A431 can be determined by clonogenic assays as described in Goldmacher et al, 102 *J. Cell Biol.* 1312-1319 (1986).

The present invention also provides a therapeutic composition comprising:

(A) an effective amount of one or more taxanes linked to a cell binding agent, and (B) a pharmaceutically acceptable carrier, diluent, or excipient.

Similarly, the present invention provides a method for killing selected cell populations comprising contacting target cells or tissue containing target cells with an effective amount of a cytotoxic agent comprising one or more taxanes linked to a cell binding agent.

The cytotoxic agent is prepared as described above.

Suitable pharmaceutically acceptable carriers, diluents, and excipients are well known and can be determined by those of ordinary skill in the art as the clinical situation warrants.

Examples of suitable carriers, diluents and/or excipients include: (1) Dulbecco's phosphate buffered saline, pH about 7.4, containing or not containing about 1 mg/ml to 25 mg/ml human serum albumin, (2) 0.9% saline (0.9% w/v NaCl), and (3) 5% (w/v) dextrose; and may also contain an antioxidant such as tryptamine and a stabilizing agent such as Tween 20.

The method for killing selected cell populations can be practiced in vitro, in vivo, or ex vivo.

Examples of in vitro uses include treatments of autologous bone marrow prior to their transplant into the same patient in order to kill diseased or malignant cells: treatments of bone marrow prior to their transplantation in order to kill competent T cells and prevent graft-versus-host-disease (GVHD); treatments of cell cultures in order to kill all cells except for desired variants that do not express the target antigen; or to kill variants that express undesired antigen.

The conditions of non-clinical in vitro use are readily determined by one of ordinary skill in the art.

Examples of clinical ex vivo use are to remove tumor cells or lymphoid cells from bone marrow prior to autologous transplantation in cancer treatment or in treatment of autoimmune disease, or to remove T cells and other lymphoid cells from autologous or allogenic bone marrow or tissue prior to transplant in order to prevent GVHD. Treatment can be carried out as follows. Bone marrow is harvested from the patient or other individual and then incubated in medium containing serum to which is added the cytotoxic agent of the invention, concentrations range from about 10 μM to 1 pM, for about 30 minutes to about 48 hours at about 37° C. The exact conditions of concentration and time of incubation, i.e., the dose, are readily determined by one of ordinary skill in the art. After incubation the bone marrow cells are washed with medium containing serum and returned to the patient intravenously according to known methods. In circumstances where the patient receives other treatment such as a course of ablative chemotherapy or total-body irradiation between the time of harvest of the marrow and reinfusion of the treated cells, the treated marrow cells are stored frozen in liquid nitrogen using standard medical equipment.

For clinical in vivo use, the cytotoxic agent of the invention will be supplied as a solution or a lyophilized powder that are tested for sterility and for endotoxin levels. Examples of suitable protocols of conjugate administration are as follows. Conjugates are given weekly for 4 weeks as an intravenous bolus each week. Bolus doses are given in 50 to 100 ml of normal saline to which 5 to 10 ml of human serum albumin can be added. Dosages will be 10 μg to 2000 mg per administration, intravenously (range of 100 ng to 20 mg/kg per day). After four weeks of treatment, the patient can continue to receive treatment on a weekly basis. Specific clinical protocols with regard to route of administration, excipients, diluents, dosages, times, etc., can be determined by one of ordinary skill in the art as the clinical situation warrants.

Examples of medical conditions that can be treated according to the in vivo or ex vivo methods of killing selected cell populations include malignancy of any type including, for example, cancer of the lung, breast, colon, prostate, kidney, pancreas, ovary, and lymphatic organs; autoimmune diseases, such as systemic lupus, rheumatoid arthritis, and multiple sclerosis; graft rejections, such as renal transplant rejection, liver transplant rejection, lung transplant rejection, cardiac transplant rejection, and bone marrow transplant rejection; graft versus host disease; viral infections, such as CMV infection, HIV infection, AIDS, etc.; and parasite infections, such as giardiasis, amoebiasis, schistosomiasis, and others as determined by one of ordinary skill in the art.

EXAMPLES

The invention will now be illustrated by reference to non-limiting examples. Unless otherwise stated, all percents, ratios, parts, etc. are by weight.

Example 1

In Vitro Cytotoxicity Assays

The sulfide, disulfide, and sulfhydryl containing taxane drugs of the invention can be evaluated for their ability to suppress proliferation of various human tumor cell lines in vitro. Two adherent cell lines A431 (human epidermoid carcinoma) and SKBR3 (human breast tumor) and the non-adherent cell line, Namalwa (Burkitt's lymphoma) are used for the assessment of cytotoxicity of these compounds. Cells are exposed to the compounds for 24 hours and the surviving fractions of cells are measured in direct assays. (A431 and SKBR3 are assayed for plating efficiency (Goldmacher et al, 102 *J. Cell. Biol.* 1312-1319 (1986) and Namalwa are assayed by growth back extrapolation (Goldmacher et al, 135 *J. Immunol.* 3648-3651 (1985)). $IC_{50}$ values are then calculated from this data.

Example 2

Conjugation to Antibodies

Conjugation of Thiol-containing Taxane to Antibodies via Disulfide Links: The conjugation of thiol-containing taxanes to antibodies, or fragments thereof, via disulfide links is performed in two steps. In the first step dithiopyridyl groups are introduced into antibodies or antibody fragments using succinimidyl pyridyldithiopentanoate (SPP) as described by Carlsson et al. The thiopyridyl groups are then displaced by reaction with the thiol-containing taxane to produce a conjugate.

Preparation of Antibody-SS-Taxane Conjugates. Antibodies anti-B4, anti-EGF receptor and N901, or fragments thereof, are modified with SPDP or SPP as described in the literature. Between 1 to 10 dithiopyridyl groups are introduced on the average per antibody molecule.

A solution of the dithiopyridyl modified antibody at a concentration of 1 mg/ml in 0.1 M potassium phosphate buffer pH 6.5 containing 1 mM EDTA at 25° C. is treated with a thiol-containing taxane (1.25 molar equivalent/dithiopyridyl group). The release of thiopyridine from the modified antibody or fragment thereof is monitored spectrophotometrically at 343 nm and is found to be complete in about 20 hours. The antibody-taxane conjugate is purified and freed of unreacted drug and other low molecular weight material by gel filtration through a column of Sephadex G-25. The number of taxane molecules bound per antibody molecule is determined by measuring the ratio between the absorbances at 230 nm and 275 nm. An average of 1-10 taxane molecules per antibody molecule can be linked via disulfide bonds by this method.

Conjugation of Thiol-Containing Taxane to Antibodies via a Noncleavable Thioether Link: The conjugation of a thiol-containing taxane is performed in two steps. The antibody, or fragment thereof, is first reacted with succinimidyl maleimidomethylcyclohexane carboxylate (SMCC) to introduce maleimido groups. The modified antibody is then reacted with the thiol-containing taxane forming thioether links.

Preparation of Antibody-Taxane Conjugates (non-cleavable). Antibodies, anti-B4, anti-EGF receptor and N901, or fragments thereof, are modified with SMCC as described in the literature.

The modified antibodies or antibody fragments are treated with thiol-containing taxane (1.25 molar equivalent/maleimido group). The mixtures are incubated overnight at 4° C. The antibody-taxane conjugates are purified as described above. Typically, an average of 1-10 taxane molecules per antibody molecule are linked.

Specific Preparation of Antibody-Taxane Conjugates

Murine monoclonal antibodies directed against the human EGF receptor (EGFR) were developed. The EGF receptor is known to be over-expressed in several human squamous cell cancers, such as, head and neck, lung and breast. Four different antibodies, KS-61 (IgG2a), KS-77 (IgG1), KS-78 (Ig2a), and KS-62 (IgG2a) were linked to taxanes via disulfide bonds. The murine monoclonal antibody TA1, directed against the neu oncogene over-expressed in human breast and ovarian cancers, was used for the preparation of TA1-taxane conjugates. The preparation of these particular conjugates is described in Examples 3 through 7.

Example 3

Preparation Of Anti-EGFR Antibody KS-61-Taxane Conjugate

The anti-EGFR antibody KS-61 was first modified with N-succinimidyl-4-[2-pyridyldithio]pentanoate (SPP) to introduce dithiopyridyl groups. The antibody (2.3 mg/mL) in 50 mM potassium phosphate buffer, pH 6.5, containing NaCl (50 mM) and EDTA (2 mM), was treated with SPP (11 molar equivalents in ethanol). The final ethanol concentration was 1.4% (v/v). After 90 minutes at ambient temperature, lysine (50 mM) was added to help in the removal of any non-covalently bound SPP. The reaction was allowed to proceed for two hours, and then purified by gel filtration through a Sephadex G25 column equilibrated in the above buffer. Antibody-containing fractions were pooled and the degree of modification was determined by treating a sample with dithiothreitol and measuring the change in absorbance at 343 nm (release of pyridine-2-thione with $\epsilon_{343}$=8,080 $M^{-1}$ $cm^{-1}$). Recovery of the antibody was about 90%, with 5.0 pyridyldithio groups linked per antibody molecule.

The modified antibody was diluted with 50 mM potassium phosphate buffer, pH 6.5, containing NaCl (50 mM) and EDTA (2 mM) to a final concentration of 1.28 mg/mL. Taxane-SH (1.7 eq. per dithiopyridyl group) in ethanol (10% v/v in final reaction mixture) was then added to the modified antibody solution. The reaction proceeded at ambient temperature under argon for 24 hours. The progress of the reaction was monitored spectrophotometrically at 343 nm for release of pyridine-2-thione, caused by disulfide exchange between the taxane-SH and the dithiopyridyl groups on the antibody. The increase in absorbance at 343 nm indicated that the taxane had linked to the antibody. The reaction mixture was then loaded on to a Sephadex G25 SF gel filtration column equilibrated with phosphate-buffered saline (PBS, pH 6.5) containing 20% propylene glycol. The major peak comprised monomeric KS-61-Taxane. The concentration of the conjugate was determined by measuring the absorbance at 280 nm. The conjugate was formulated with Tween 80 (0.05%) and human serum albumin (HSA, 1 mg/mL).

Example 4

Preparation Of Anti-EGFR Antibody KS-77-Taxane Conjugate

The anti-EGFR antibody KS-77 was modified with N-succinimidyl-4-[2-pyridyldithio]pentanoate (SPP) to introduce dithiopyridyl groups. The antibody (5.0 mg/mL) in 50 mM potassium phosphate buffer, pH 6.5, was treated with SPP (11 molar equivalents in ethanol). The final ethanol concentration was 2% (v/v). After 90 minutes at ambient temperature, lysine (50 mM) was added to help in the removal of any non-covalently bound SPP. The reaction mixture was allowed to incubate for two hours, and then purified by gel filtration through a Sephadex G25 column equilibrated in the above buffer. Antibody containing fractions were pooled and the degree of modification was determined by treating a sample with dithiothreitol and measuring the change in absorbance at 343 nm (release of 2-mercaptopyridine with $\epsilon_{343}$=8,080 $M^{-1}$ $cm^{-1}$). Recovery of the antibody was about 90%, with 4.24 pyridyldithio groups linked per antibody molecule.

The modified antibody was diluted with 50 mM potassium phosphate buffer, pH 6.5, containing NaCl (50 mM) and EDTA (2 mM) to a final concentration of 1.4 mg/mL. Taxane-SH (1.7 equivalents per dithiopyridyl group) in ethanol (10% v/v in final reaction mixture) was then added to the modified antibody solution. The reaction proceeded at ambient temperature under argon for 24 hours. An increase in absorbance at 343 nm was noted, indicating that pyridine-2-thione was being released, and the taxane had linked to the antibody. The reaction mixture was then loaded on to a Sephacryl S300HR gel filtration column equilibrated with phosphate-buffered saline (PBS, pH 6.5). The major peak comprised monomeric KS-77-Taxane. The concentration of antibody KS-77 was determined by measuring the absorbance at 280 nm. The conjugate was formulated with Tween 80 (0.06%) and HSA (1 mg/mL).

Example 5

Preparation Of Anti-EGFR Antibody KS-62-Taxane Conjugate

The anti-EGF antibody-taxane conjugate (KS-62-Taxane) was prepared in a manner similar to that described in Example 4. The modified antibody was diluted with 50 mM potassium phosphate buffer, pH 6.5, containing NaCl (50 mM) and EDTA (2 mM) to a final concentration of 2.5 mg/mL. The antibody was modified with SPP to introduce 5.25 pyridyldithio groups per antibody molecule Taxane-SH (1.7 eq.) in ethanol (10% v/v in final reaction mixture) was then added to the modified antibody solution. The reaction proceeded at ambient temperature under argon for 24 hours. The conjugate was purified by passage through a Sephacryl S300HR gel filtration column equilibrated with phosphate-buffered saline (PBS, pH 6.5). The major peak comprised monomeric KS-62-Taxane. The conjugate was formulated in PBS, containing Tween 80 (0.01%, w/v) and HSA (1 mg/mL).

Example 6

Preparation Of Anti-EGFR Antibody KS-78-Taxane Conjugate

The anti-EGFR antibody-Taxane conjugate, KS-78-Taxane, was prepared in a manner similar to that described in Example 4. The modified antibody was diluted with 50 mM potassium phosphate buffer, pH 6.5, containing NaCl (50 mM) and EDTA (2 mM) to a final concentration of 1.6 mg/mL. The antibody was modified with SPP to introduce 4.0 pyridyldithio groups per antibody molecule. Taxane-SH (1.7 eq.) in ethanol (15% v/v in final reaction mixture) was then added to the modified antibody solution. The reaction proceeded at ambient temperature under argon for 24 hours. The solution was then split into two batches, Batch A and Batch B, which were treated separately. Batch A was dialyzed against PBS, pH 6.5 containing 2 mM CHAPS (3-[(cholamidopropyl)dimethylammonio]-1-propanesulfonate) and 20% (v/v) propylene glycol. The pH of the final solution was 6.0. Batch B was dialyzed into PBS, pH 6.5 containing 20% (v/v) propylene glycol. After dialyses, HSA (1 mg/mL) was added to both batches. Batch B was further treated with Tween 80 (0.05%, w/v).

Example 7

Preparation Of TA1-Taxane Conjugate

The murine monoclonal antibody TA 1, which binds to the neu oncogene expressed on breast and ovarian tumors, was used in the preparation of a taxane conjugate. TA1 (3.2 mg/mL) in 50 mM potassium phosphate buffer, pH 6.5, containing NaCl (50 mM) and EDTA (2 mM) was treated with SPP (8.0 molar equivalents in ethanol). The final ethanol concentration was 5% (v/v). After 90 minutes at ambient temperature, lysine (50 mM) was added to help in the removal of any non-covalently bound SPP. The reaction mixture was incubated for 2 hours, and then gel filtered through a Sephadex G25 column equilibrated in the above buffer. Antibody-containing fractions were pooled and the degree of modification was determined by treating a sample with dithiothreitol and measuring the change in absorbance at 343 nm (release of pyridine-2-thione with $\epsilon_{343}$=8,080 $M^{-1}$ $cm^{-1}$). Recovery of the antibody was about 90%, with 4.9 pyridyldithio groups linked per antibody molecule.

The modified antibody was diluted with 50 mM potassium phosphate buffer, pH 6.5, containing NaCl (50 mM) and EDTA (2 mM) to a final concentration of 1.0 mg/mL. Taxane-SH (1.7 eq. per pyridyldithio group incorporated) in ethanol (10% v/v in final reaction mixture) was then added to the modified antibody solution. The reaction proceeded at ambient temperature under argon for 24 hours. The release of pyridine-2-thione (monitored at 343 nm), indicated that the disulfide exchange between the Taxane-SH and the pyridyldithio substituent on the antibody was complete. A portion of the reaction mixture (4.0 mg) was then loaded on a Sephacryl S300HR gel filtration column equilibrated with phosphate-buffered saline (PBS, pH 6.5). The major peak comprised monomeric TA1-Taxane. The remaining conjugate was diluted to 0.5 mg/mL, and dialyzed into 50 mM potassium phosphate buffer, pH 6.5, containing NaCl (50 mM), EDTA (2 mM) and 20% propylene glycol. The concentration of antibody TA1 was determined in both species by measuring the absorbance at 280 nm. The conjugates were formulated in PBS containing Tween 80 (0.01%) and HSA (1 mg/mL).

Example 8

Other Methods of Linking Taxanes

Acid Labile Linkers

Taxanes can be esterified with N-protected amino acids, such as N-tboc-L-alanine in the presence of dicyclohexylcarbodiimide and dimethylaminopyridine (DMAP) by standard methods described in the chemical literature. Cleavage of the t-boc protecting group with trifluoroacetic acid will give a taxane ester containing a terminal amino group. This amino group containing taxane can be linked to antibodies, or fragments thereof, and other cell binding agents via an acid labile linker as previously described (Blättler et al, 24 *Biochemistry*, 1517-1524 (1985), U.S. Pat. Nos. 4,542,225, 4,569,789 and 4,764,368).

Photolabile Linker

The amino group-containing taxane derivative described above can be linked to cell binding agents via a photolabile linker as previously described. (Senter et al, 42 *Photochemistry and Photobiology*, 231-237 (1985), U.S. Pat. No. 4,625,014).

Peptidase Labile Linker

The amino group-containing taxane described above can also be linked to cell binding agents via peptide spacer linkers. It has been previously shown that short peptide spacers between drugs and macromolecular protein carriers are stable in serum but are readily hydrolyzed by intracellular lysosomal peptidases (Trouet et al, 79 *Proc. Nat'l. Acad. Sci.*, 626-629 (1982)). The amino group containing taxane can be condensed with peptides such as Ala-Leu, Leu-Ala-Leu or a dimer of Ala-Leu using condensing agents such as 1-[3-(dimethylamino)propyl]-3-ethyl carbodiimide-HCl to give a peptide derivative of the taxane which can then be linked to cell binding agents.

Esterase Labile Linker

Taxanes can be esterified by reaction of the hydroxyl group with succinic anhydride and then linked to a cell binding agent to produce a conjugate that can be cleaved by intracellular esterases to liberate free drug. (For examples, see: Aboud-Pirak et al, 38 *Biochem. Pharmacol.*, 641-648 (1989), Laguzza et al, 32 *J. Med. Chem.*, 549-555 (1989)).

Example 9

In Vivo Anti-Tumor Activity

The anti-tumor effect of anti-EGF receptor antibody-taxane conjugate on human squamous cancer (A431) xenografts in SCID mice was established as follows. The anti-tumor effect of two different anti-human epidermal growth factor receptor-taxane conjugates (anti-EGFR-taxane conjugates), KS-61-Taxane and KS-77-Taxane was evaluated in a human tumor xenograft model in SCID mice.

Five week old female SCID mice (25 animals) were inoculated subcutaneously in the right flank with A-431 human squamous cancer cells ($1.5 \times 10^6$ cells/mouse) in 0.1 mL of serum-free medium. The tumors were grown for 11 days to an average size of 100.0 $mm^3$ (range of 54-145 $mm^3$). The animals were then randomly divided into four groups (3 to 5 animals per group) according to their tumor size. The first group received KS-61-Taxane conjugate (10 mg/kg, qd×5) administered intravenously. The second group received the KS-77-Taxane conjugate (10 mg/kg, qd×5) administered intravenously. The third group received free (non-conjugated) taxane (0.24 mg/kg, qd×5, intravenously) at the same dose as that present in the conjugate. The fourth group, a control group, of animals received PBS using the same treatment schedule as in groups 1-3.

Figure 4:
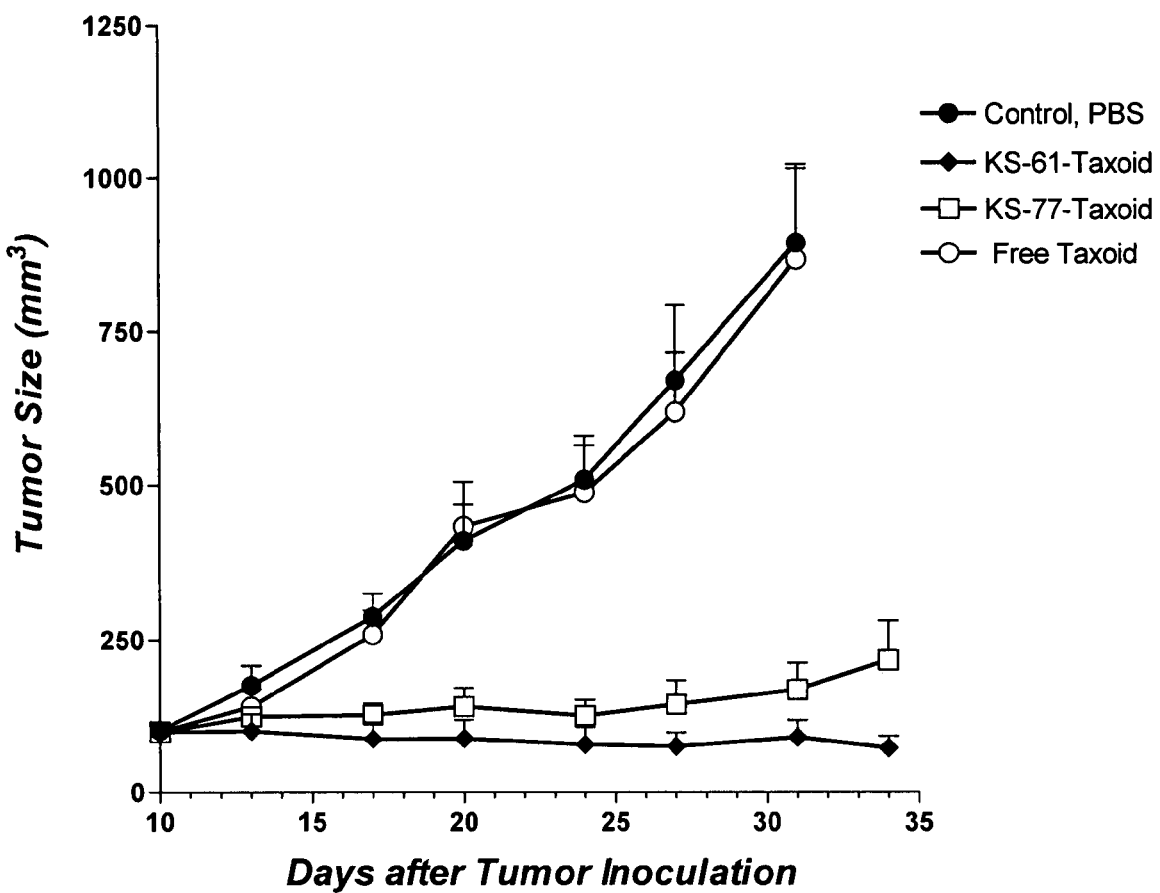
FIG. 4 shows the anti-tumor effect of anti-EGF Receptor Antibody-Taxane Conjugate on human squamous cancer (A431) xenografts in SCID mice.
Figure 5:
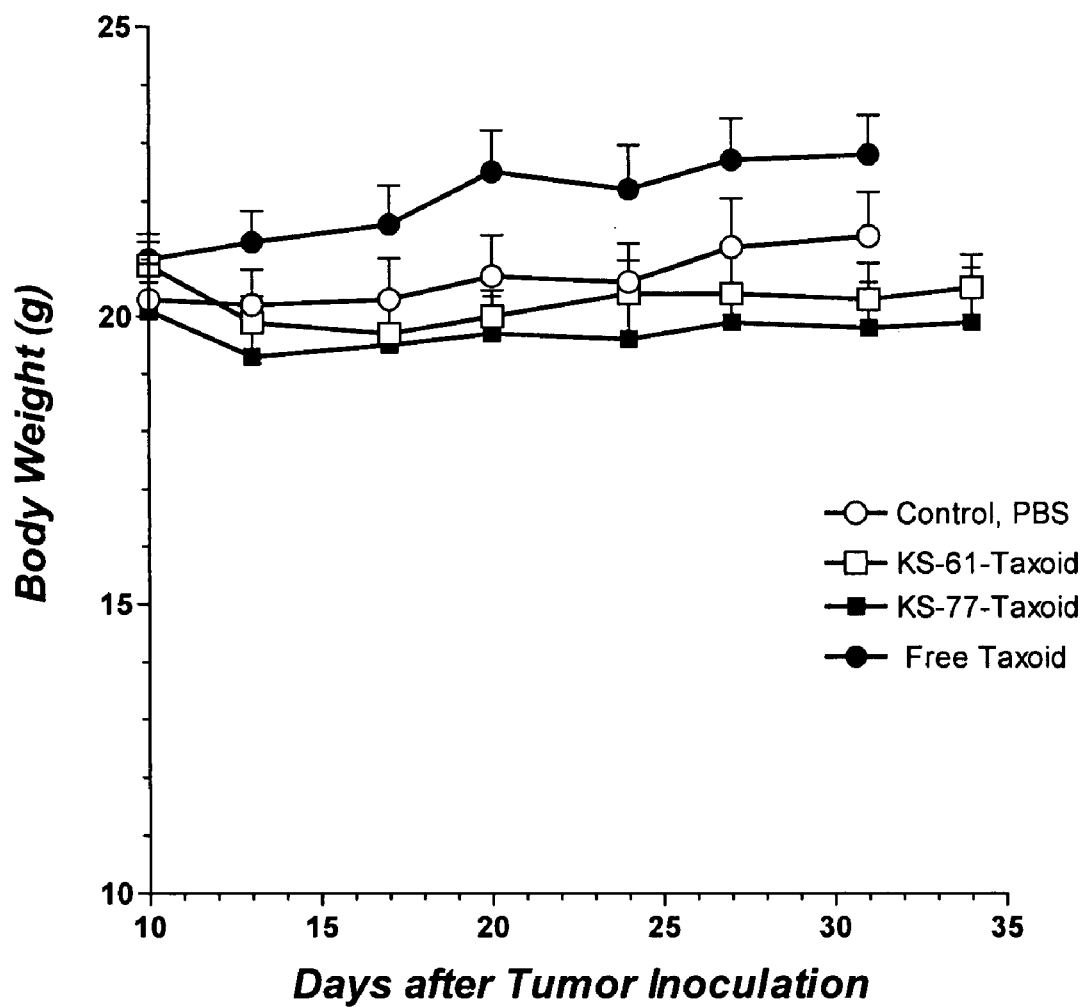
FIG. 5 shows the body weight change of the SCID mice used in the experiment described in Example 10.

The sizes of the tumors were measured twice weekly and the tumor volumes were calculated with the formula: ½ (length ×width×height). The weight of the animals was also measured twice per week. The results are shown in FIGS. 4 and 5. The tumors in the control group of mice grew to a size of nearly 1000 $mm^3$ in 31 days. Treatment with free taxane showed no therapeutic effect, and the tumors in this group grew at essentially the same rate as in the control group of animals that received PBS.

In contrast, both of the anti-EGFR-taxane conjugates showed remarkable anti-tumor activity resulting in complete inhibition of tumor growth in all the treated animals for the duration of the experiment—34 days for the KS-61-Taxane conjugate and 27 days for the KS-77-Taxane conjugate. The data also show that targeted delivery of the taxane using a tumor-specific antibody is essential for the anti-tumor activity, since an equivalent dose of unconjugated taxane showed no anti-tumor effect in this model. Importantly, the doses of antibody-taxane conjugate used were non-toxic to the animals as demonstrated by the absence of any weight loss (see FIG. 5).

Example 10

In Vitro Cytotoxicity of Antibody-Taxane Conjugates

The cytotoxicity of anti-EGFR-taxane conjugate, KS-78-Taxane, was measured in a clonogenic assay using the EGFreceptor-positive human A431 cell line (ATCC CRL 1555). N901-taxane conjugate, a similar conjugate made with the mouse monoclonal N901 antibody against human CD56 was tested as a specificity control, since A431 cells do not express its target antigen, CD56. The cytotoxicity of TA.1-Taxane conjugate, a conjugate made with the mouse monoclonal antibody TA.1 against human Neu antigen, was measured on the antigen-positive human cell line SK-BR-3 (ATCC HTB 30) and the antigen-negative A431 cell line. Cells were plated at different densities in 6-well tissue-culture plates in DMEM medium supplemented with 10% fetal calf serum. Immunoconjugates at varying concentrations were added and the cells were maintained in a humidified atmosphere at 37° C. and 6% $CO_2$ until colonies of approximately 20 cells or more were formed (6 to 10 days). Control plates contained no immunoconjugate. The cells were then fixed with formaldehyde, stained with crystal violet, and counted under a low-magnification microscope. Plating efficiencies were then determined from the colony numbers and surviving fractions of cells were calculated as the ratio of the plating efficiency of the treated sample and the plating efficiency of the control.

Figure 6:
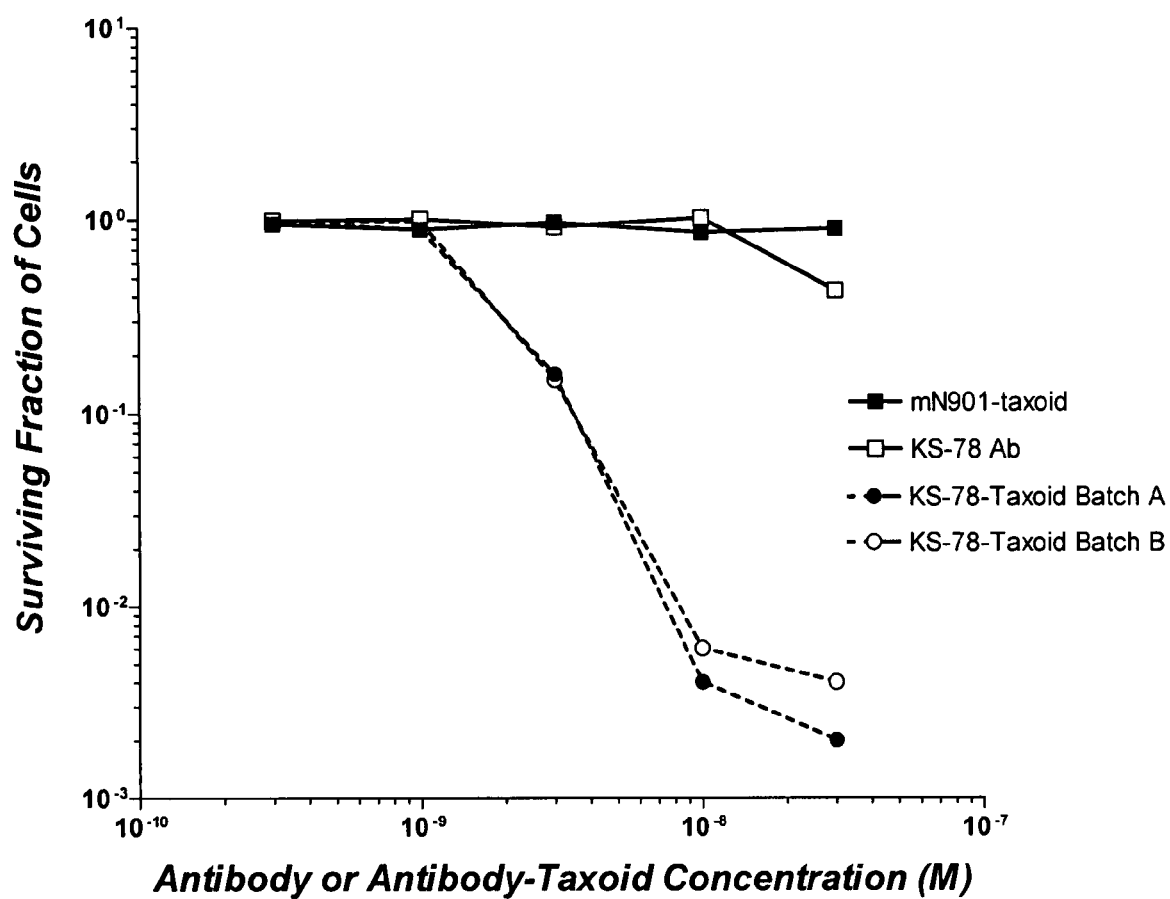
FIG. 6 shows the results of a cytotoxicity determination for the anti-EGF receptor-taxane conjugate on the target antigen-positive cell line A431 and for the N901-taxane conjugate for which the A431 cell line does not express the target antigen.

FIG. 6 shows the results of the cytotoxicity determination for the two Batches of KS-78-Taxane conjugate on the target antigen-positive cell line A431. Conjugates from both batches show similar toxicity to the target cells; treatment for 6 days at concentrations of $10^{-8}$ M achieved surviving fractions of less than $10^{-2}$ (less than 1% of cells survive). A control conjugate, N901-Taxane, for which there are no antigens present on the surface of A431 cells, shows no toxicity to the cells at concentrations of up to $3 \times 10^{-8}$ M. Unconjugated KS-78 antibody also shows very little cytotoxic effect. These results demonstrate the target antigen-specific cytotoxicity of the KS-78-taxane conjugate.

Figure 7:
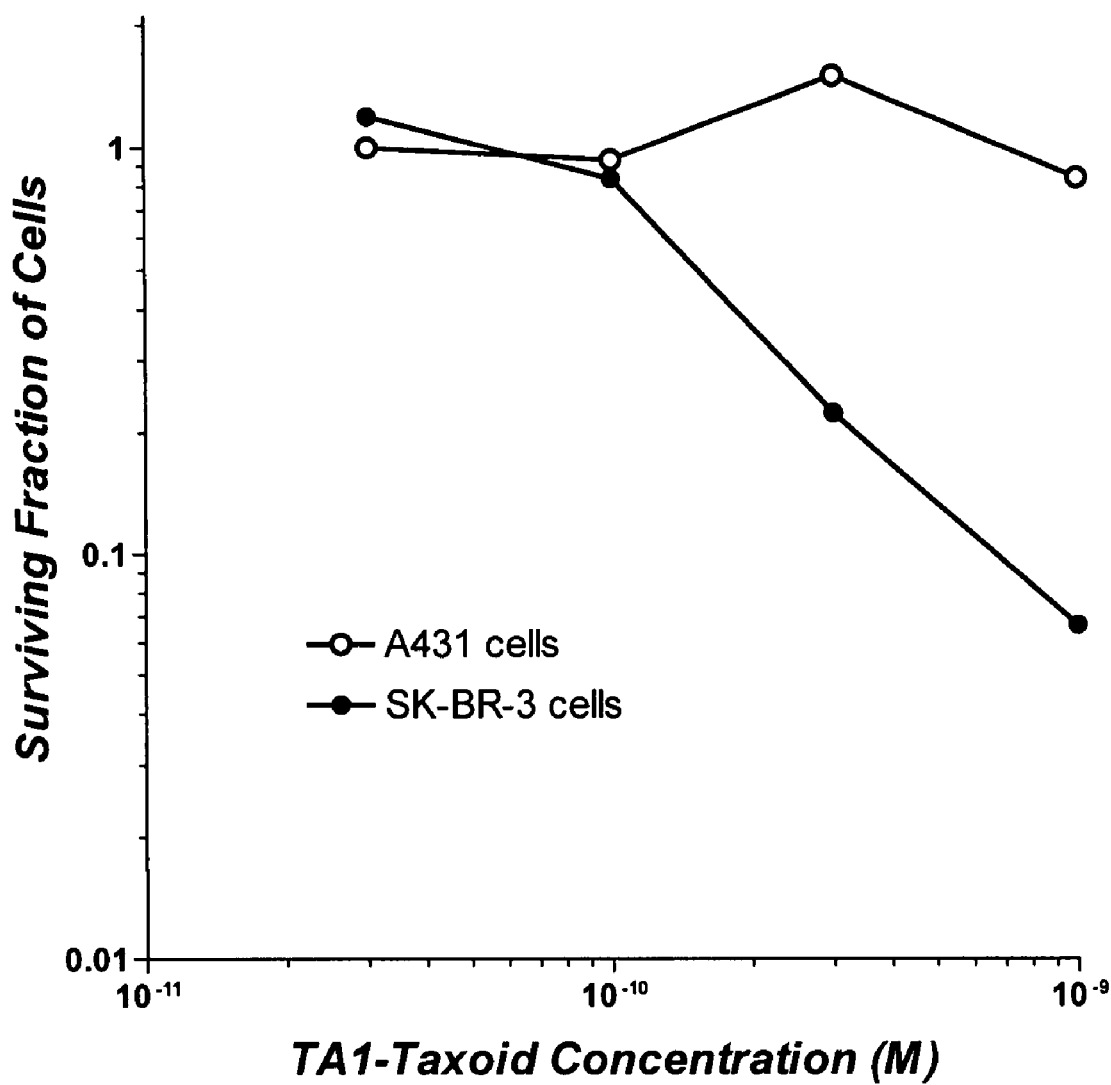
FIG. 7 shows the cytotoxic potency and selectivity of the TA.1-taxane conjugate in the target antigen-positive cell line SK-BR-3 and the target antigen-negative cell line A431.

The cytotoxic potency and selectivity of the TA.1-taxane conjugate was assayed with the target antigen-positive cell line SK-BR-3 and the target antigen-negative cell line A431. The results are shown in FIG. 7. At a conjugate concentration of $10^{-9}$ M, more than 90% of the target SK-BR-3 cells were killed (surviving fraction of less than 0.1), while no toxicity towards the non-target A431 cells was observed. These results demonstrate the selective killing of antigen-positive cells and that the cytotoxic effect of the conjugate is dependent on the specific binding through its antibody component.

While the invention has been described in detail and with reference to specific embodiments thereof, it will be apparent to one of ordinary skill in the art that various changes and modifications can be made therein without departing from the spirit and scope of the invention.

What is claimed is:

1. A method for inducing cell death in selected cell populations comprising contacting target cells or tissue containing target cells with an effective amount of a cytotoxic agent, wherein the cytotoxic agent is one or more taxanes covalently bonded to a cell binding agent through a linking group, wherein at least one of said taxanes is a compound represented by formula (I):

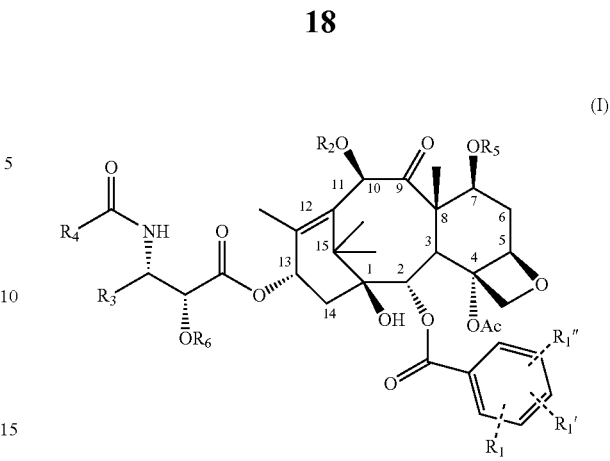

wherein:
$R_1''$ is H,
$R_1$ and $R_1'$ are the same or different and are F, $NO_2$, CN, Cl, $CHF_2$, $CF_3$, $-NR_7R_8$ or $-OR_9$ wherein $R_7$ and $R_8$ are the same or different and are linear alkyl having 1 to 10 carbon atoms, branched or cyclic alkyl having 3 to 10 carbon atoms, or simple or substituted phenyl or naphthyl and $R_9$ is linear alkyl having 1 to 10 carbon atoms, or branched or cyclic alkyl having 3 to 10 carbon atoms;
$R_2$ is $-CONR_{10}R_{11}$, wherein $R_{10}$ and $R_{11}$ are the same or different and are H, linear alkyl having 1 to 10 carbon atoms, branched or cyclic alkyl having 3 to 10 carbon atoms, or aryl;
$R_3$ is aryl, linear alkyl having 1 to 10 carbon atoms, or branched or cyclic alkyl having 3 to 10 carbon atoms;
$R_4$ is $-OC(CH_3)_3$ or phenyl;
$R_5$ is $-(CH_2)_nSZ$, $-CO(CH_2)_nSZ$, $-(CH_2)_nCH(CH_3)SZ$, $-CO(CH_2)_nCH(CH_3)SZ$, $-(CH_2)_nC(CH_3)_2SZ$, $-CO(CH_2)_nC(CH_3)_2SZ$, $-CONR_{12}(CH_2)_nSZ$, $-CONR_{12}(CH_2)_nCH(CH_3)SZ$, $-CONR_{12}(CH_2)_nC(CH_3)_2SZ$, $-CO$-morpholino-XSZ, $-CO$-piperidino-XSZ, $-CO$-piperazino-XSZ, or $-CO-N$-methylpiperazino-XSZ, wherein
Z is H or SR, wherein R and $R_{12}$ are the same or different and are linear alkyl having 1 to 10 carbon atoms, branched or cyclic alkyl having 3 to 10 carbon atoms, or simple or substituted phenyl, naphthyl or heterocyclic, and $R_{12}$ in addition can be H,
X is linear alkyl having 1 to 10 carbon atoms or branched alkyl having 3 to 10 carbon atoms, and
n is an integer of 1 to 10; and
$R_6$ is H;
wherein the target cells express a marker that binds to the cell binding agent, and
wherein the target cells are human cancer cells.

2. The method of claim 1, wherein one or both of $R_1$ and $R_1'$ are $-OCH_3$ or $-OCH_2CH_3$.

3. The method of claim 1, wherein $R_7$ and $R_8$ each has 1 to 4 carbon atoms.

4. The method of any one of claims 1, 2 and 3, wherein $R_7$ and $R_8$ are the same.

5. The method of claim 1, wherein $R_2$ is $-CONHCH_2CH_3$, $-CO$-morpholino, $-CO$-piperidino, $-CO$-piperazino, or $-CO-N$-methylpiperazino.

6. The method of claim 1, wherein the cell binding agent is selected from the group consisting of antibodies, an antigen specific antibody fragment, interferons, lymphokines, hormones, vitamins, growth factors, colony stimulating factors, and nutrient-transport molecules.

7. The method of claim 6, wherein the cell binding agent is an antibody or an antigen specific antibody fragment thereof.

8. The method of claim 6, wherein the cell binding agent is a monoclonal antibody or an antigen specific antibody fragment thereof.

9. The method of claim 8, wherein the cell binding agent is specific for Common Acute Lymphoblastic Leukemia Antigen (CALLA) or CD19 antigen.

10. The method of claim 8, wherein the monoclonal antibody is monoclonal antibody J5 or an anti-B4 monoclonal antibody.

11. The method of claim 8, wherein the antigen specific antibody fragment is selected from the group consisting of sFV, Fab, Fab', and F(ab')$_2$.

12. The method of claim 6, wherein the cell binding agent is an interferon.

13. The method of claim 12, wherein the interferon is interferon α, interferon β or interferon γ.

14. The method of claim 6, wherein the cell binding agent is a lymphokine.

15. The method of claim 14, wherein the lymphokine is IL-2, IL-3, IL-4 or JL-6.

16. The method of claim 6, wherein the cell binding agent is a hormone.

17. The method of claim 16, wherein the hormone is insulin, thyrotropin releasing hormones (TRH), thyroid stimulating hormone (TSH), melanocyte-stimulating hormone (MSH), or a steroid hormone.

18. The method of claim 17, wherein the steroid hormones are androgens, androgen analogues, estrogens or estrogen analogues.

19. The method of claim 17, wherein the steroid hormones are estradiol or androstenediol.

20. The method of claim 6, wherein the cell binding agent is a vitamin.

21. The method of claim 20, wherein the vitamin is folic acid.

22. The method of claim 6, wherein the cell binding agent is a growth factor.

23. The method of claim 22, wherein the growth factor is epidermal growth factor (EGF) or transforming growth factor α (TGF-α)

24. The method of claim 6, wherein the cell binding agent is a colony stimulating factor.

25. The method of claim 24, wherein the colony stimulating factor is G-CSF, M-CSF or GM-CSF.

26. The method of claim 6, wherein the cell binding agent is a nutrient-transport molecule.

27. The method of claim 26, wherein the nutrient-transport molecule is a transferrin.

28. The method of claim 1, wherein the cancer cells are solid tumor cells.

29. The method of claim 1, wherein the target cells are lung, breast, colon, prostate, kidney, pancreas, ovary, or lymphatic cancer cells.

* * * * *